United States Patent
Yong et al.

(10) Patent No.: US 9,518,125 B2
(45) Date of Patent: Dec. 13, 2016

(54) COMPOSITION FOR DIAGNOSING LIVER CANCER AND METHODS OF DIAGNOSING LIVER CANCER AND OBTAINING INFORMATION FOR DIAGNOSING LIVER CANCER

(71) Applicant: Samsung Electronics Co., Ltd., Suwon-si, Gyeonggi-do (KR)

(72) Inventors: Ye-ryoung Yong, Seoul (KR); Hyun-ju Kang, Hwaseong-si (KR); Ga-hee Kim, Yongin-si (KR); Kyung-hee Park, Seoul (KR); Jong-myeon Park, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/322,570

(22) Filed: Jul. 2, 2014

(65) Prior Publication Data
US 2015/0104879 A1   Apr. 16, 2015

(30) Foreign Application Priority Data

Oct. 15, 2013  (KR) .................. 10-2013-0122962

(51) Int. Cl.
| | | |
|---|---|---|
| *G01N 31/00* | (2006.01) | |
| *G01N 33/53* | (2006.01) | |
| *C07K 16/30* | (2006.01) | |
| *C07K 16/28* | (2006.01) | |

(52) U.S. Cl.
CPC ......... *C07K 16/303* (2013.01); *C07K 16/2896* (2013.01)

(58) Field of Classification Search
CPC .............. A61K 2039/6025; C12Q 1/6886; C12Q 2600/158; C12Q 2600/178; G01N 33/57434
See application file for complete search history.

(56) References Cited

U.S. PATENT DOCUMENTS

| | | |
|---|---|---|
| 2010/0151480 A1 | 6/2010 | Taylor et al. |
| 2010/0255514 A1 | 10/2010 | Rak et al. |
| 2011/0166200 A1 | 7/2011 | Zhang et al. |
| 2011/0236903 A1* | 9/2011 | McClelland ......... C12Q 1/6886 435/6.14 |
| 2012/0214689 A1 | 8/2012 | Croce et al. |
| 2012/0289418 A1* | 11/2012 | Willard-Gallo ...... C12Q 1/6883 506/9 |
| 2013/0045220 A1 | 2/2013 | Oliner et al. |
| 2013/0131194 A1 | 5/2013 | Skog et al. |
| 2013/0244256 A1 | 9/2013 | Clarke et al. |
| 2013/0287772 A1 | 10/2013 | Halbert et al. |
| 2014/0141986 A1* | 5/2014 | Spetzler ............... C12Q 1/6886 506/9 |

FOREIGN PATENT DOCUMENTS

| | | |
|---|---|---|
| KR | 2010-127768 A | 12/2010 |
| KR | 2013-0056855 A | 10/2013 |

OTHER PUBLICATIONS

Orozco and Lewis (Cytometry A, Jun. 2010, vol. 77, No. 6, pp. 502-514).*
Tascilar et al. (Annals of Oncology 10,Suppl. 4:S107-S110, 1999).*
Tockman et al. (Cancer Research 52:2711s-2718s, 1992).*
Strating et al., The p24 family and selective transport processes at the ER-Golgi interface, *Biol. Cell*, 101: 495-509 (2009).

* cited by examiner

*Primary Examiner* — Lisa Cook
(74) *Attorney, Agent, or Firm* — Leydig, Voit & Mayer, Ltd.

(57) ABSTRACT

Provided is method of diagnosing liver cancer in a subject, the method comprising contacting a sample from a subject with a substance that specifically binds to transmembrane emp24 domain trafficking protein 2 (TMED2), cluster of differentiation 43 (CD43), or any combination thereof on the surface of a microvesicle; and measuring the level of the substance bound to microvesicles in the sample; and related methods and compositions.

6 Claims, 4 Drawing Sheets

COMPOSITION FOR DIAGNOSING LIVER CANCER AND METHODS OF DIAGNOSING LIVER CANCER AND OBTAINING INFORMATION FOR DIAGNOSING LIVER CANCER

RELATED APPLICATION

This application claims the benefit of Korean Patent Application No. 10-2013-0122962, filed on Oct. 15, 2013 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 17,898 bytes ASCII (Text) file named "716092_ST25.TXT," created Jun. 30, 2014.

BACKGROUND OF THE INVENTION

1. Field

The present disclosure relates to compositions for diagnosing liver cancer in a subject and methods of diagnosing liver cancer and obtaining information for diagnosing liver cancer in a subject.

2. Description of the Related Art

When it is difficult or impracticable to perform a biopsy to diagnose a disease such as cancer, a diagnostic method using biological fluids such as blood, urine, or saliva may be employed. However, due to the absence of a high accuracy marker, there are difficulties in diagnosing diseases such as cancer using biological fluids. In the case of diagnosing liver cancer, alpha-fetoprotein (AFP) is a widely known plasma protein that can be used as a marker, but AFP has a low sensitivity for detection of liver cancer. In addition, AFP levels are increased in patients with cirrhosis as well. Accordingly, it is difficult to use patients' AFP levels to detect progression from cirrhosis to liver cancer.

When a biopsy is used to diagnose cancer, a patient may suffer from an invasive procedure such as an incision. Also, when an error occurs during sampling of a specimen for examination, the diagnostic accuracy may be low.

Transmembrane emp24 domain trafficking protein 2 (TMED2) is a protein encoded in humans by the TMED2 gene. Research indicates that TMED2 specifically binds to Golgi reassembly-stacking protein 1 (GORASP1) and Golgi reassembly-stacking protein 1 (GORASP2).

Cluster of differentiation 43 (CD43), which is also known as sialophorin (SPN) or leukosialin, is a transmembrane cell surface protein encoded in humans by the SPN gene. CD43 is a major sialoglycoprotein on the surface of human T lymphocytes, monocytes, granulocytes, and some B lymphocytes, wherein CD43 appears to be important for the immune function. CD 43 may be a part of a physiologic ligand-receptor complex involved in T-cell activation.

However, there is no evidence that TMED2 and/or CD43 is associated with liver cancer.

BRIEF SUMMARY OF THE INVENTION

A method of diagnosing liver cancer in a subject, the method comprising contacting a sample from a subject with a substance that specifically binds to transmembrane emp24 domain trafficking protein 2 (TMED2), cluster of differentiation 43 (CD43), or any combination thereof on the surface of a microvesicle; measuring the level of the substance bound to microvesicles in the sample; measuring the level of the substance bound to microvesicles in the control sample; and determining that the subject has a liver cancer or an increased likelihood of developing a liver cancer when the level of the substance bound to microvesicles in the sample is equal to or greater than a threshold level, or when the level of the substance bound to microvesicles in the sample is greater than the highest level among levels obtained from the plurality of samples obtained from cirrhosis patients, wherein the control sample includes a plurality of samples obtained from liver cancer patients and a plurality of samples obtained from cirrhosis patients, and the threshold level is a value such that the probability of a sample to be a liver cancer patient is equal to or greater than 50% to 100% and the probability of a sample to be a liver cancer patient is obtained by analyzing the measured level with a statistic model. Other methods and related compositions are also provided.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION OF THE INVENTION

Figure 1:
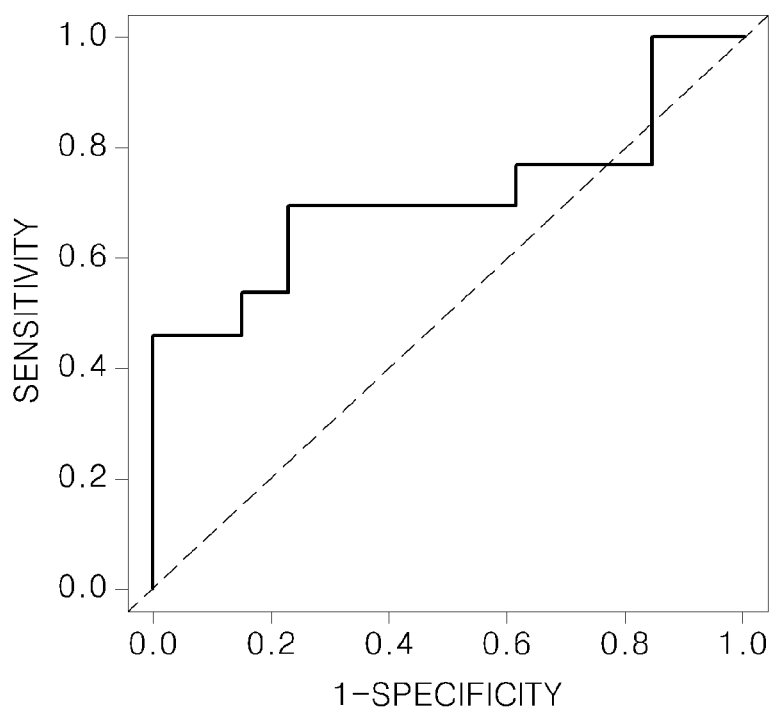
FIG. 1 is a graph showing a receiver operating characteristic (ROC) curve for determining the presence of cirrhosis or liver cancer in a sample based on band intensity values of protein measured in microvesicles that are separated by using beads coated with anti-transmembrane emp24 domain trafficking protein 2 (TMED2)

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

According to one aspect of the present disclosure, provided is a composition for diagnosing liver cancer in a subject, wherein the composition includes a substance that specifically binds to transmembrane emp24 domain trafficking protein 2 (TMED2), cluster of differentiation 43 (CD43), or a combination thereof.

TMED2 is a protein encoded in human by the TMED2 gene. Research indicates that TMED2 specifically binds to Golgi reassembly-stacking protein 1 (GORASP1) and Golgi reassembly-stacking protein 2 (GORASP2). TMED2 may have an amino acid sequence of NP_006806 (SEQ ID NO: 1) and be encoded by a nucleotide sequence of NM_006815 (SEQ ID NO: 2).

CD43, which is also known as sialophorin (SPN) or leukosialin, is a transmembrane cell surface protein that in human is encoded by SPN gene. CD43 is a major sialoglycoprotein on the surface of human T lymphocytes, monocytes, granulocytes, and some B lymphocytes, wherein CD43 appears to be important for immune function. CD43 may be a part of a physiologic ligand-receptor complex involved in T-cell activation. CD43 may have an amino acid sequence of NP_001025459 (SEQ ID NO: 3) and be encoded by a nucleotide sequence of NM_001030288 (SEQ ID NO: 4).

The TMED2, CD43, or combination thereof may be present in microvesicles, for example, on the surface of the microvesicles derived from a living body. The TMED2, CD43, or combination thereof may be present specifically on the surface of microvesicles that are separated from a subject with liver cancer. The TMED2, CD43, or combination thereof may be present at higher amounts on the surface of the microvesicles that are separated from the subject with liver cancer than on the surface of microvesicles that are separated from a control group sample. The control group sample may comprise samples from one or more normal subjects, one or more subjects with a disease other than liver cancer, for example, cirrhosis, or a combination thereof. The control sample may include a plurality of samples obtained from liver cancer patients and a plurality of samples obtained from cirrhosis patients. In this regard, the composition may be used to distinguish the subject with liver cancer from the control group, for example subjects with cirrhosis. A positive control also can be used (e.g., the level of TMED2, CD43, or both in samples from one or more known positive liver cancer subjects), in which case a lower level of the biomarkers can indicate that the test subject does not have liver cancer. Furthermore, the control (the level of TMED2, CD43, or both in a sample from a known non-cancerous subject or a known cancerous subject) can be provided in the form of empirical measurements from such known samples taken before, during, or after measurements of the test sample, or the control can be provided by pre-determined levels of TMED2, CD43, or both (e.g., levels from a known cancerous or non-cancerous sample or average level of multiple such samples previously determined and stored in any form, such as a comparison scale generated from such measurements or data in a non-transitory storage medium.

The microvesicles may be separated from the subject with liver cancer or the subject with cirrhosis according to methods known in the art. The methods may include a process of centrifuging the sample, a process of filtering the sample, a process of incubating the microvesicles with a substance that specifically binds thereto or that is intercalated between a lipid bilayer, or any combination thereof. The incubation may be carried out in vitro. In addition, examples of the separation methods of the microvesicles include a process using a solid support or centrifugal forces, density gradient centrifugation, ultracentrifugation, filtration, dialysis, immunoaffinity chromatography, electrophoresis, or any combination thereof. The substance that specifically binds to the microvesicles may be a substance capable of binding to surface proteins, lipids, or sugars of the microvesicles. Examples of the surface proteins of the microvesicles include CD63, CD83, CD9, integrin-beta 1 (ITGB1), EpCAM, caveolin, FasL, HLA-DRA, CD36, CD63, CD81, MUC1, ERBB4, GPER, ERBB2, MLANA, AMHR2, or any combination thereof. The substance that specifically binds to the microvesicles may be a substance having binding affinity to proteins, such as an enzyme substrate, a coenzyme, a regulatory factor, or a substance that specifically binds to receptors, such as lectin, a sugar, a glycoprotein, an antigen, an antibody or a antigen-binding fragment thereof such as an Fab fragment, a hormone, a neurotransmitter, a phospholipid-binding protein, a pleckstrin homology (PH) domain-containing protein, a cholesterol-containing protein, or any combination thereof. The Fab fragment comprises antigen-binding sites, and examples of the Fab fragment include a single-domain antibody, a Fab, a Fab', and a scFv. The substance that is intercalated between the lipid bilayer may include a lipophilic moiety, an amphipathic moiety, a moiety of zwitterions, or any combination thereof. Examples of the lipophilic moiety include fatty acid, sterol, or glyceride. Examples of the amphipathic moiety include phospholipid or sphingolipid. Examples of the moiety of zwitterions include sulfobetaine, carboxybetaine, or phosphoryl choline. The substance that specifically binds to the microvesicles or that is intercalated between the lipid bilayer may bind to a solid support. The solid support may have a shape of a sphere, polygon, plate, a linear shape, or any combination thereof. The solid support may be formed of polystyrene, polypropylene, magnetic particles, or any combination thereof.

The sample may be biological materials derived from the subject. Such biological material may include a solid tissue obtained from a fresh or preserved organ or a tissue sample, or by a biopsy; blood or blood components; amniotic fluid, peritoneal fluid; bodily fluid such as interstitial fluid; cells; or any combination thereof. The sample may include compounds, such as a preservative, an anti-coagulant, a buffer, a fixative, a nutrient, and antibiotics, wherein the compounds are not naturally mixed with the biological material. Examples of the biological sample include urine, mucus, saliva, tears, blood, plasma, serum, sputum, spinal fluid, pleural effusion, nipple aspirates, lymph fluid, airway fluid, intestinal fluid, urogenital duct fluid, breast milk, semen, cerebrospinal fluid, bodily fluid of organ system, peritoneal fluid, bodily fluid of cystic tumor, amniotic fluid, or any combination thereof. The sample may also include circulating tumor cells (CTCs). The substance that specifically binds to TMED2, CD43, or combination thereof may also specifically bind to TMED2, CD43, or combination thereof on the surface of the microvesicles that are separated from the living body.

The substance that specifically binds to TMED2, CD43, or combination thereof may be a material that naturally or non-naturally binds to TMED2, CD43, or combination thereof. The substance that may naturally bind to TMED2, CD43, or combination thereof may be, for example, a protein that specifically binds to TMED2, CD43, or combination thereof within the living body. Examples of the substance that specifically binds to the TMED2, CD43, or combination thereof include an antibody or a antigen binding fragment thereof, a ligand, a substrate, an inhibitor, an agonist, an antagonist, a co-factor, or any combination thereof. The antibody may be a monoclonal antibody or a polyclonal antibody. The antigen binding fragment of the antibody may be a single-domain antibody, a Fab, a Fab', a scFv, or any combination thereof.

The substance that specifically binds to TMED2, CD43, or combination thereof may be attached to a detectable label. The detectable label may be primary labels where the label comprises an element that is detected directly or that produces a directly detectable label, or secondary labels where the detected label binds to a primary label, as is common in immunological labeling. The detectable label may include an optical label, an electrical label, a radioactive label, an enzyme label, or any combination thereof. The enzyme may be an enzyme converting a substrate to directly detectable labels. The enzyme may be a horse radish peroxidase, alkaline phosphatase, luciferase, etc. The secondary labels may include biotin, streptavidin, digoxigenin, primary antibodies etc. The optical label may be a fluorescent substance or a phosphorescent substance. Examples of the fluorescent substance include fluorescein, rhodamine, cyanine (Cy), metalloporphyrin complex, Cy-5, and Cy-3. Examples of the fluorescein dye include 6-carboxyfluorescein (6-FAM), 1,2', 4',1,4,-tetrachlorofluorescein (TET) 2 and 2',4',5',7',1,4-hexachlorofluorescein (HEX) 3,2',7' dimethoxy-4',5'-dichloro-6-carboxyrhodamine (JOE) 4,2'-chloro-5'-fluoro-7', 8'-fused phenyl-1,4-dichloro-6-carboxyfluorescein 5, and 2'-chloro-7'-phenyl-1,4-dichloro-6-carboxyfluorescein 6.

The substance that specifically binds to TMED2, the CD43, or a combination thereof may be fixed to a solid support. The solid support may be formed of nanoparticles or microparticles. The solid support may be formed of magnetic particles or non-magnetic particles. The solid support may have a shape of a bead, a sphere, a polygon, a plate, or any combination thereof. The solid support may be in the form of an array to which the substance that specifically binds to TMED2, CD43, or combination thereof is fixed in a certain area.

The composition may further include a reagent to measure expression levels of micro RNA (mir)-210, mir-346, or a combination thereof. The reagent may specifically bind to mir-210, mir-346, or a combination thereof, or may bind to nucleotide sequences each complementary to mir-210, mir-346, or a combination thereof. The reagent may be a natural substance, a synthetic substance, or a semi-synthetic substance. The reagent may include nucleic acid, for example, DNA, RNA, DNA-RNA hybrid, PNA, or any combination thereof. The nucleic acid may be single, double or multi stranded. The nucleic acid may include 10 nucleotides (nt) or more in length. For example, the nucleic acid may include about 10 nt to about 1,000 nt, about 10 nt to about 500 nt, about 10 nt to about 100 nt, about 10 nt to about 50 nt, about 10 nt to about 30 nt, about 10 nt to about 20 nt, about 15 nt to about 100 nt, about 15 nt to about 50 nt, about 15 nt to about 30 nt, about 15 nt to about 20 nt, about 20 nt to about 1,000 nt, about 20 nt to about 500 nt, about 20 nt to about 100 nt, about 20 nt to about 50 nt, about 20 nt to about 30 nt, about 30 nt to about 1,000 nt, about 30 nt to about 500 nt, about 30 nt to about 100 nt, about 30 nt to about 50 nt, about 40 nt to about 100 nt, about 40 nt to about 80 nt, or about 40 nt to about 60 nt in length.

The reagent may include a primer, a probe or an antisense sequence containing a sequence specific to mir-210 or a complementary sequence thereof. The reagent may also include a primer, a probe or an antisense sequence containing a sequence specific to mir-346 or a complementary sequence thereof. The reagent may also include any combination of primers, probes or antisense sequences containing a sequence specific or complementary to mir-210 or mir-346. The primer may serve as a polymerization start site for a polymerase in a polymerase chain reaction (PCR). The primer may be used in a nucleic acid amplification reaction. The term "amplification" used herein refers to a method of amplifying copies of a target sequence or a complementary sequence thereof. The nucleic acid amplification reaction may be carried out by any method known in the art. The nucleic acid may be amplified through multiple cycles during the amplification reaction, or may be amplified in a single temperature or temperature range with a cycle. Examples of cycling techniques used in the nucleic acid amplification reaction include, for example, a method relying on a thermal cycling. The method using the thermal cycling may include PCR. PCR is widely known in the art and includes a process of denaturation in which double-stranded DAN is denatured into single-stranded DNA by thermal denaturation; a process of annealing in which a primer is annealed to the single-stranded DNA; and a process of elongation in which a new DNA strand complementary to the single-stranded DNA is synthesized and elongated from the primer. A method of isothermal amplification of nucleic acid is a method carried out in a single temperature or temperature range without a cycle, or is a method relying on main aspects of the amplification process in a single temperature. In contrast to the PCR in which a reaction product is heated to bind to an additional primer for the separation of double-stranded DNA, the method of isothermal amplification of nucleic acid involves a strand displacing polymerase to separate double-stranded DNA and re-copy a template single-stranded DNA. In order to initiate reiterative template copying, the method of isothermal amplification of nucleic acid may be divided into a method relying on the strand displacing polymerase and the other method relaying on continuous reuse or new synthesis of a single primer molecule. The strand displacing polymerase-dependent method may be selected from the group consisting of helicase dependant amplification (HAD), exonuclease dependant amplification, recombinase polymerase amplification (RPA), and loop mediated amplification (LAMP). The method relying on continuous reuse or new synthesis of the single primer molecule may be selected from the group consisting of strand displacement amplification (SDA) and nucleic acid based amplification (NASBA and TMA). The primer may include one or at least two primer sets according to the selected method. The primer may be a primer used for the PCR.

Mir-210 is a mature microRNA having a nucleotide sequence of SEQ ID NO: 5, and mir-346 is a mature microRNA having a nucleotide sequence of SEQ ID NO: 6.

The reagent may be attached to a detectable label. The detectable label is defined as described above. The reagent may be fixed to glass or a solid support. The solid support is defined as described above.

The composition may be in any phase. That is, the composition may be in a liquid phase, a solid phase, or a combination thereof.

The subject may be a mammal, and the mammal may be a human, a mouse, a cow, a pig, a horse, a sheep, a dog, a cat, or any combination thereof.

The composition described above may be used for the performance of the method described hereinafter.

According to another aspect of the present invention, there is provided a kit for diagnosing liver cancer in a subject by using the composition that includes the substance specifically binding to TMED2, CD43, or combination thereof.

The substance that specifically binds to TMED2, CD43, or combination thereof is defined as described above. A kit may further include a reagent for diagnosing liver cancer in a subject, and the reagent may include a buffer, an indicator, or a combination thereof. The kit described above may be used for the performance of the method described hereinafter.

According to another aspect of the present invention, there is provided a method of diagnosing liver cancer in a subject, the method including contacting a sample from the subject to a substance that specifically binds to TMED2, CD43, or combination thereof on the surface of microvesicles in the sample; measuring the level of the substance bound to microvesicles in the sample; measuring the level of the substance bound to microvesicles in the control sample; and determining that the subject has a liver cancer or an increased likelihood of developing a liver cancer when the level of the substance bound to microvesicles in the sample is equal to or greater than a threshold level, or when the level of the substance bound to microvesicles in the sample is greater than the highest level among levels obtained from the plurality of samples obtained from cirrhosis patients, wherein the control sample includes a plurality of samples obtained from liver cancer patients and a plurality of samples obtained from cirrhosis patients, and the threshold level is a value such that the probability of a sample to be a liver cancer patient is equal to or greater than 50% to 100% and the probability of a sample to be a liver cancer patient is obtained by analyzing the measured level with a statistic model. The threshold level may be a value such that the probability of a sample to be a liver cancer patient is equal to or greater than 50% to 100%, for example, 50% to 90%, 50% to 80%, 50% to 70%, 50% to 60%, 60% to 100%, 70% to 100%, 80% to 100%, 90% to 100%, 60% to 90%, 60% to 80%, 60% to 70%, 70% to 90%, 70% to 80%, 55%, 60%, 65%, 70%, 75%, 80%, 85%, 90%, 95%, or 100%.

The contacting may be carried out in a liquid medium. The liquid medium may include a liquid sample itself, water, a buffer, or any combination thereof. The contacting may be carried out by mixing the sample with the substance. In some embodiments, the contacting may be carried out by stirring the mixture containing the sample and the substance, wherein the stirring may be carried out to a certain extent that does not destroy microvesicles contained therein.

The subject may be a mammal, and the mammal may be a primate. Additional examples of the mammal include a human, a mouse, a cow, a pig, a horse, a sheep, a dog, a cat, or any combination thereof.

The sample may comprise biological materials derived from the subject. The biological material may include solid tissue obtained from a fresh or preserved organ or tissue sample, or by a biopsy; blood or blood components; amniotic fluid, peritoneal fluid; bodily fluid such as interstitial fluid; cells; or any combination thereof. The sample may include compounds, such as a preservative, an anti-coagulant, a buffer, a fixative, a nutrient, and antibiotics, wherein the compounds are not naturally mixed with the biological material. Examples of the biological sample include urine, mucus, saliva, tears, blood, plasma, serum, sputum, spinal fluid, pleural effusion, nipple aspirates, lymph fluid, airway fluid, intestinal fluid, urogenital duct fluid, breast milk, semen, cerebrospinal fluid, bodily fluid of organ system, peritoneal fluid, bodily fluid of cystic tumor, amniotic fluid, or any combination thereof. The sample may also include CTCs.

The TMED2, CD43, or combination thereof may be associated with microvesicles, for example, on the surface of the microvesicles derived from the living body. The TMED2, CD43, or combination thereof may be present specifically on the surface of microvesicles that are separated from the subject with liver cancer. The TMED2, the CD43, or combination thereof may be present at higher levels (e.g., higher amounts) in the microvesicles that are separated from the subject with liver cancer than in microvesicles that are separated from the control group. The control group sample may be derived from one or more normal, non-cancerous subjects, one or more subjects with a disease other than liver cancer, for example, cirrhosis, or a combination thereof. In this regard, the composition may be used to distinguish the subject with liver cancer from normal subjects or subjects with cirrhosis. A positive control also can be used (e.g., the level of TMED2, CD43, or both in samples from one or more known positive liver cancer subjects), in which case a lower level of the biomarkers can indicate that the test subject does not have liver cancer. Furthermore, the control (the level of TMED2, CD43, or both in a sample from a known non-cancerous subject or a known cancerous subject) can be provided in the form of empirical measurements from such known samples taken before, during, or after measurements of the test sample, or the control can be provided by pre-determined levels of TMED2, CD43, or both (e.g., levels from a known cancerous or non-cancerous sample or average level of multiple such samples previously determined and stored in any form, such as a comparison scale generated from such measurements or data in a non-transitory storage medium.

The substance that specifically binds to TMED2, CD43, or combination thereof may be a natural or non-natural (synthetic) material that binds to TMED2, CD43, or combination thereof. The natural substance that may bind to TMED2, CD43, or combination thereof may be, for example, a protein that specifically binds to TMED2, CD43, or combination thereof within the living body. Examples of the substance that specifically binds to TMED2, CD43, or combination thereof include an antibody or a antigen binding fragment thereof, a ligand, a substrate, an inhibitor, an agonist, an antagonist, a co-factor, or any combination thereof. The antibody may be a monoclonal antibody or a polyclonal antibody. The antigen binding fragment of the antibody may be a single-domain antibody, a Fab, a Fab', a scFv, or any combination thereof. The anti-TMED2 antibody may be TMED2 (A-8) (Cat. no. sc-376033: Santa Cruz Biotechnology, Inc.), TMED2 (C-8) (Cat. no. sc-376459: Santa Cruz Biotechnology, Inc.), TMED2 (H-108) (Cat. no. sc-292002: Santa Cruz Biotechnology, Inc.), or anti-TMED2 antibody (ab97600: Abcam®). The anti-CD43 antibody may be mouse anti-CD43 antibody (Cat. no. LS-B3775, LS-B2792, LS-C134435, or LS-C87781: Lifesapn Biosciences), mouse anti-CD43 antibody (Cat. no. 10-220-C100, 1F-220-T100, 1P-220-T100, or A4-220-T100: EXBIO Antibodies), mouse anti-CD43 antibody (Cat. no. ABIN351514, ABIN260269, ABIN180650, or ABIN96680: antibodies-online.com), or anti-CD43 monoclonal antibody (Cat. No.: FAB2038P: R&D Systems, Inc.).

The substance that specifically binds to TMED2, CD43, or combination thereof may be attached to a detectable label. The detectable label may be primary labels where the label comprises an element that is detected directly or that produces a directly detectable label, or secondary labels where the detected label binds to a primary label, as is common in immunological labeling. The detectable label may include an optical label, an electrical label, a radioactive label, an enzyme label, or any combination thereof. The enzyme may be an enzyme converting a substrate to directly detectable labels. The enzyme may be a horse radish peroxidase, alkaline phosphatase, luciferase, etc. The secondary labels may include biotin, streptavidin, digoxigenin, primary antibodies etc. The optical label may be a fluorescent substance or a phosphorescent substance. Examples of the fluorescent substance include fluorescein, rhodamine, cyanine (Cy), metalloporphyrin complex, Cy-5, and Cy-3. Examples of the fluorescein dye include 6-carboxyfluorescein (6-FAM), 1,2', 4',1,4,-tetrachlorofluorescein (TET) 2 and 2',4',5',7',1,4-hexachlorofluorescein (HEX) 3,2',7' dimethoxy-4',5'-dichloro-6-carboxyrhodamine (JOE) 4,2'-chloro-5'-fluoro-7', 8'-fused phenyl-1,4-dichloro-6-carboxyfluorescein 5, and 2'-chloro-7'-phenyl-1,4-dichloro-6-carboxyfluorescein 6.

The substance that specifically binds to TMED2, CD43, or a combination thereof may be fixed to a solid support. The solid support may be formed of nanoparticles or microparticles. The solid support may be formed of magnetic particles or non-magnetic particles. The solid support may have a shape of a bead, a sphere, a polygon, a plate, or any combination thereof. The solid support may be in the form of an array to which the substance that specifically binds to the TMED2, CD43, or a combination thereof is fixed in a certain area.

The method also includes the measuring of the levels of the substance bound to the microvesicles in the sample and control sample. The measuring may be carried out by determining the presence of the substance or measuring an amount of the substance when the substance is bound to the microvesicles. The substance may be attached to a detectable label, and accordingly measurement may be carried out by measuring the amount of the substance based on signals generated from the label. The measuring may be also carried out by determining the presence of the substance or measuring the amount of the substance, after the substance is separated from the composite (i.e., product) containing the substance and the microvesicles.

The substance that specifically binds to the TMED2, CD43, or combination thereof may be attached to a detectable label. The detectable label may include an optical label, an electrical label, a radioactive label, an enzyme label, or any combination thereof. The optical label may be a fluorescent substance or a phosphorescent substance. Examples of the fluorescent substance include fluorescein, rhodamine, cyanine (Cy), metalloporphyrin complex, Cy-5, and Cy-3. Examples of the fluorescein dye include 6-carboxyfluorescein (6-FAM), 1,2',4',1,4,-tetrachlorofluorescein (TET) 2 and 2',4',5',7',1,4-hexachlorofluorescein (HEX) 3,2',7' dimethoxy-4',5'-dichloro-6-carboxyrhodamine (JOE) 4,2'-chloro-5'-fluoro-7',8'-fused phenyl-1,4-dichloro-6-carboxyfluorescein 5, and 2'-chloro-7'-phenyl-1,4-dichloro-6-carboxyfluorescein 6.

The measuring of the levels of the substance may include a process of measuring directly an amount of the substance that is separated from the microvesicles, or a process of measuring indirectly an amount of the substance without separating it from the microvesicles. The measuring may be carried out by detecting signals generated from the detectable label labeled to the substance. Means of separating the substance may include centrifugation, precipitation, salting out, dialysis, filtration, chromatography, or any combination thereof. The chromatography may include affinity chromatography, size-exclusion chromatography, ion exchange chromatography, or any combination thereof. The measuring may be carried out by ELISA, western blotting, electrophoresis, mass spectrometry, spectrometer, or any combination thereof.

The method may further include, after the contacting the sample with the substance that specifically binds TMED2 or CD43 (or both), a process of separating the microvesicles from the sample. During the process of separating the microvesicles, the microvesicles specifically bound to the substance that specifically binds to the TMED2, CD43, or combination thereof are separated from the rest of the sample. The separating of the microvesicles may be carried out by using a material such as an antibody that specifically binds to the substance that specifically binds to TMED2, CD43, or a combination thereof. The substance-specific material such as an antibody may be fixed to a solid support, for example, magnetic particles or a plate. Separation of the microvesicles may include a process of contacting the composite, containing the microvesicles and the substance, to the material, fixed to the solid support, that is specifically bound with the substance specifically binding to TMED2, CD43, or combination thereof.

Separation of the microvesicles may include a process of centrifuging the sample, a process of filtering the sample, a process of incubating the microvesicles with a substance that specifically binds thereto or that is intercalated between a lipid bilayer, or any combination thereof. The incubation may be carried out in vitro. In addition, examples of the separation methods of the microvesicles include a process using a solid support or centrifugal forces, density gradient centrifugation, ultracentrifugation, filtration, dialysis, immunoaffinity chromatography, electrophoresis such as free flow electrophoresis, or any combination thereof. The substance that specifically binds to the microvesicles may be a substance capable of binding to surface proteins, lipids, or sugars of the microvesicles. Examples of the surface proteins of the microvesicles include CD63, CD83, CD9, integrin-beta 1 (ITGB1), EpCAM, caveolin, FasL, HLA-DRA, CD36, CD63, CD81, MUC1, ERBB4, GPER, ERBB2, MLANA, AMHR2, or any combination thereof. The substance that specifically binds to the microvesicles may be a substance having binding affinity to proteins, an enzyme substrate, a coenzyme, a regulatory factor, and a substance that specifically binds to receptor, lectin, sugar, a glycoprotein, an antigen, an antibody or a antigen-binding fragment thereof, a hormone, a neurotransmitter, a phospholipid-binding protein, a pleckstrin homology (PH) domain-containing protein, a cholesterol-containing protein, or any combination thereof. The antigen binding fragment has antigen-binding sites, and examples of the antigen binding fragment include a single-domain antibody, a Fab, a Fab', and a scFv. The substance that is intercalated between the lipid bilayer may include a lipophilic moiety, an amphipathic moiety, a moiety of zwitterions, or any combination thereof. Examples of the lipophilic moiety include fatty acid, sterol, or glyceride. Examples of the amphipathic moiety include phospholipid or sphingolipid. Examples of the moiety of zwitterions include sulfobetaine, carboxybetaine, or phosphoryl choline. The substance that specifically binds to the microvesicles or that is intercalated between the lipid bilayer may bind to a solid support. The solid support may have a shape of sphere, polygon, plate, linear, or any combination thereof. The solid support may be formed of polystyrene, polypropylene, magnetic particles, or any combination thereof.

The method may further include a process of separating the microvesicles from the sample that is separated from the subject, before contacting with the substance that specifically binds to TMED2, CD43. In this step, the substance that specifically binds to TMED2, CD43, or combination thereof may not be used. Accordingly, the substance that specifically binds to TMED2, CD43, or combination thereof may enable to measure an amount of the microvesicles that are present on the surface with respect to the whole microvesicles. The separation of the microvesicles is defined as described above.

The method includes determining that the subject has a liver cancer or an increased likelihood of developing a liver cancer when the level of the substance bound to microvesicles in the sample is equal to or greater than a threshold level, or when the level of the substance bound to microvesicles in the sample is greater than the highest level among levels obtained from the plurality of samples obtained from cirrhosis patients, wherein the control sample includes a plurality of samples obtained from liver cancer patients and a plurality of samples obtained from cirrhosis patients, and the threshold level is a value such that the probability of a sample to be a liver cancer patient is equal to or greater than 50% to 100% and the probability of a sample to be a liver cancer patient is obtained by analyzing the measured level with a statistic model. The statistic model may be linear regression model, a logistic regression model, etc. The threshold level may be a value such that the probability of a sample to be a liver cancer patient is equal to or greater than 50% to 100%, for example, 50% to 90%, 50% to 80%, 50% to 70%, 50% to 60%, 60% to 100%, 70% to 100%, 80% to 100%, 90% to 100%, 60% to 90%, 60% to 80%, 60% to 70%, 70% to 90%, 70% to 80%, 55%, 60%, 65%, 70%, 75%, 80%, 85%, 90%, 95%, or 100%. The probability of a sample to be a liver cancer patient may be determined by a linear predictor function derived from a logistic regression model. The basic idea of logistic regression is to use the mechanism already developed for linear regression by modeling the probability pi using a linear predictor function, i.e., a linear combination of the explanatory variables and a set of regression coefficients that are specific to the model at hand but the same for all trials. The linear predictor function f(i) for a particular data point I is written as:

$$f(i)=\beta_0+\beta_1\chi_{1,i}+\ldots+\beta_m\chi_{m,i},$$

where $\beta_0, \ldots, \beta_m$ are regression coefficients indicating the relative effect of a particular explanatory variable on the outcome.

The linear predictor function may be obtained by using, for example, a cross-validation method. Cross-validation, sometimes called rotation estimation, is a model validation technique for assessing how the results of a statistical analysis will generalize to an independent data set. It is mainly used in settings where the goal is prediction, and one wants to estimate how accurately a predictive model will perform in practice. It is worth highlighting that in a prediction problem, a model is usually given a dataset of known data on which training is run (training dataset), and a dataset of unknown data (or first seen data) against which the model is tested (testing dataset). The goal of cross validation is to define a dataset to "test" the model in the training phase (i.e., the validation dataset), in order to limit problems like overfitting, give an insight on how the model will generalize to an independent data set (i.e., an unknown dataset, for instance from a real problem), etc. One round of cross-validation involves partitioning a sample of data into complementary subsets, performing the analysis on one subset (called the training set), and validating the analysis on the other subset (called the validation set or testing set). To reduce variability, multiple rounds of cross-validation are performed using different partitions, and the validation results are averaged over the rounds. Cross-validation is important in guarding against testing hypotheses suggested by the data (called "Type III errors"), especially where further samples are hazardous, costly or impossible to collect. The cross-validation method may includes K-fold cross-validation, 2-fold cross-validation, leave-one-out cross-validation. As the name suggests, leave-one-out cross-validation (LOOCV) involves using a single observation from the original sample as the validation data, and the remaining observations as the training data. This is repeated such that each observation in the sample is used once as the validation data. This is the same as a K-fold cross-validation with K being equal to the number of observations in the original sampling.

The control sample may be a plurality of samples obtained from liver cancer patients without cirrhosis, and a plurality of samples obtained from cirrhosis patients without a liver cancer.

The method may further include a process of measuring the level of other tumor markers present in the sample or a control sample, for example in the separated microvesicles. A tumor marker may be a tumor marker of liver cancer. The term "tumor marker" used herein refers to a compound of a moiety specifically found in tumor cells or tissues other than TMED2 or CD43. The tumor marker may be a protein or nucleic acid, and the nucleic acid may be miRNA. The tumor marker may be present in microvesicles. Thus, measurement of the amount of tumor markers may include a process of directly measuring an amount of one or more tumor markers that are separated from the microvesicles, or a process of measuring indirectly an amount of one or more tumor markers without separating them from the microvesicles. Measurement may be carried out by detecting signals generated from a detectable label attached to the tumor markers. Separation of the tumor markers may be carried out by centrifugation, precipitation, salting out, dialysis, filtration, chromatography, or any combination thereof. The chromatography may include affinity chromatography, size-exclusion chromatography, ion exchange chromatography, or any combination thereof. The measuring may be carried out by ELISA, western blotting, electrophoresis, mass spectrometry, spectrometer, or any combination thereof. When the tumor marker is a nucleic acid, the tumor marker may be used to measure amplification products of the nucleic acid. Here, the amplification may include isothermal amplification or thermocycling amplification such as PCR. Nucleic acid markers such as DNA and RNA markers may require use of a probe relying on fluorescence resonance energy transfer (FRET) pairs in their measuring, and thus, the nucleic acid markers may be measured in real time at the same time as the amplification thereof. The amplification may be a real time PCR.

The method may further include a process of measuring the level of mir-210, mir-346, or a combination thereof that is present in a sample or a control sample, for example, in the separated microvesicles. The measuring may be carried out by separating mir-210, mir-346, or a combination thereof, and measuring directly an amount thereof. Alternatively, the measuring may be carried out by amplifying mir-210, mir-346, or a combination thereof, and measuring an amount thereof. Regarding the amplification, a nucleotide sequence binding to mir-210, mir-346, or a combination thereof, a nucleotide sequence complementary to mir-210, a nucleotide sequence complementary to mir-346, or a nucleotide sequence complementary to a combination of mir-210 and mir-346 may be used as a primer and/or a probe. Such a primer and/or a probe may be a natural substance, a synthetic substance, or a semi-synthetic substance. The nucleotide sequence may include, for example, DNA, RNA, DNA-RNA hybrid, PNA, or any combination thereof.

Mir-210 is mature microRNA having a nucleotide sequence of SEQ ID NO: 5, and mir-346 is mature microRNA having a nucleotide sequence of SEQ ID NO: 6.

The nucleotide sequence may be attached to a detectable label. The detectable label is defined as described above. The nucleotide sequence may be fixed to glass support or a solid support. The solid support is defined as described above.

If the amount of TMED2, CD43, mir-210, mir-346, or any combination thereof is higher in the subject sample than in a control group sample, the method may further include a process of determining that the subject has liver cancer. The control group may be derived from one or more normal subjects, one or more subjects with a disease other than liver cancer, for example, cirrhosis, or a combination thereof. In this regard, the subject with liver cancer may be distinguished from normal subjects and subjects with cirrhosis.

According to another aspect of the present invention, there is provided a method of obtaining information for diagnosing liver cancer to a subject, the method including contacting a sample separated from a subject and a substance specifically binding to TMED2, CD43, or a combination thereof wherein the sample comprises microvesicles to which the substance can bind; and measuring the amount of the substance contained in the sample.

The phrases "contacting of the sample separated from the subject to the substance specifically binding to the TMED2, the CD43, or a combination thereof" and the "measuring of the levels of the substance contained in the sample" are defined as described above.

Hereinafter, the present invention will be described in further detail with reference to the following examples. These examples are for illustrative purposes only and are not intended to limit the scope of the invention.

Example 1

Selection of a Protein Marker Specific to Liver Cancer

The presence of a marker specific to liver cancer contained in blood-derived microvesicles was confirmed using each of the samples derived from patients with cirrhosis and patients with liver cancer as explained below.

Blood samples in a range of 8 ml to 10 ml were each derived from 13 patients with cirrhosis without liver cancer and 13 patients with liver cancer without a cirrhosis, which are examined and confirmed by X-ray computed tomography (x-ray CT) scan and/or magnetic resonance imaging (MRI) scan, by using BD Vacutainer® Plus plastic whole blood tubes. X-ray CT is a technology that uses computer-processed x-rays to produce tomographic images (virtual "slices") of specific areas of the scanned object, allowing the user to see what is inside it without cutting it open. MRI is a medical imaging technique used in radiology to investigate the anatomy and function of the body in both health and disease. Then, the blood samples were separately centrifuged at 1300×g at a temperature of 4° C. for 10 minutes, and plasma was separated therefrom. The separated plasma was then stored at a temperature of −80° C. Thereafter, a plasma sample was prepared by thawing the stored plasma followed by centrifugation at 3000×g at a temperature of 4° C. for 5 minutes so as to use the supernatants, and remove any precipitates.

Three hundred microliters of the each plasma sample were mixed with 30 ul of beads (0.8 ug antibodies/bead ul) each coated with anti-CD9 antibodies (#MAB1880: R&D Systems), anti-TMED2 antibodies (#sc-376459: Santa Cruz Biotechnology), or anti-CD43 antibodies (#MAB2038: R&D Systems) by using a test tube (Axygen). Then, the mixture was incubated at room temperature for 4 hours in a Grant Bio-rotator, and the beads were separated from the mixture by using a magnetic force. Next, the separated beads were mixed again with 300 ul of PBS, followed by incubation at room temperature for 3 hours as a washing step. The antibody-coated beads were prepared as follows: The beads were used to coat protein G on Dynabead M-270 Amine according to a cross-linking reaction using NHS/EDC(N-hydroxysuccinimide/1-ethyl-3-(3-dimethylaminopropyl) carbodiimide), and then each antibody was added thereto for the reaction so as to coat thereon by using dimethylpimelimidate. As a result, $2\times10^6$ of the beads were contained in 1 ul of PBS.

After the PBS was removed, 30 ul of NuPAGE LDS sample buffer (Life Technologies), which is a lysis buffer containing lithium dodecyl sulfate with a pH value of 8.4, were added to the test tube, followed by thermal treating in a heating block at a temperature of 95° C. for 10 minutes, thereby lysing the microvesicles. The resulting lysates were subject to electrolysis followed by western blotting. The results detected in the western blotting were analyzed with luminescence images by using ImageQuant LAS 4000 min with rabbit's anti-integrin-β1 as the first antibody and HRP-conjugated anti-rabbit antibody as the second antibody. Integrin-β1 is a marker that is typically present in microvesicles.

Based on band intensity values of the integrin-β1 protein compared to those measured in the microvesicles separated by using the beads coated with anti-CD9 antibodies, the band intensity values measured in microvesicles separated by using the beads coated with anti-TMED2 antibodies or anti-CD43 antibodies were corrected (i.e., normalized). CD9 is a marker that is typically present in microvesicles, and thus, the band intensity values of the integrin-β1 protein measured in the microvesicles separated by using the beads coated with anti-CD9 antibodies denotes an amount of total microvesicles contained in a sample or an amount of integrin-β1 protein contained in the microvesicles.

The ROC curve was generated based on the band intensity values of the integrin-β1 protein measured in the microvesicles separated by using the beads coated with anti-TMED2 antibodies, anti-CD43 antibodies, or a combination thereof. Table 1 shows the band intensity values of the integrin-β1 protein measured in the microvesicles separated by using the beads coated with anti-TMED2 antibodies and the predicted co-variances.

TABLE 1

| Sample no. | *intensity | Actual disease state | ***Predict-noCV | ***Predict_noCV.prob |
|---|---|---|---|---|
| 1 | 69.84 | LC | C | 0.565479944 |
| 2 | 82.40 | LC | LC | 0.48093397 |
| 3 | 30.40 | LC | C | 0.790880377 |
| 4 | 111.34 | LC | LC | 0.297528356 |
| 5 | 114.67 | LC | LC | 0.279052124 |
| 6 | 52.16 | LC | C | 0.677358047 |

TABLE 1-continued

| Sample no. | *intensity | Actual disease state | ***Predict-noCV | ***Predict_noCV.prob |
|---|---|---|---|---|
| 7 | 88.74 | LC | LC | 0.438367291 |
| 8 | 83.71 | LC | LC | 0.472095241 |
| 9 | 138.54 | LC | LC | 0.168706157 |
| 10 | 119.96 | LC | LC | 0.251193549 |
| 11 | 162.62 | LC | LC | 0.095681062 |
| 12 | 39.91 | LC | C | 0.745168058 |
| 13 | 105.75 | LC | LC | 0.330064731 |
| 14 | 76.06 | C | C | 0.523779232 |
| 15 | 62.99 | C | C | 0.610334267 |
| 16 | 90.23 | C | LC | 0.428470602 |
| 17 | 89.19 | C | LC | 0.435372812 |
| 18 | 75.37 | C | C | 0.528432409 |
| 19 | 28.89 | C | C | 0.797555246 |
| 20 | 78.83 | C | C | 0.505065667 |
| 21 | 9.29 | C | C | 0.87003203 |
| 22 | 60.30 | C | C | 0.627493535 |
| 23 | 86.16 | C | LC | 0.455615913 |
| 24 | 62.26 | C | C | 0.615019949 |
| 25 | 76.02 | C | C | 0.524049102 |
| 26 | 81.61 | C | LC | 0.486270325 |

*"intensity" refers to band intensity values of the integrin-β1 protein measured in the microvesicles separated by using the beads coated with anti-TMED2 antibodies.
** Predict-noCV refers to a predicted normalized covariance.
******Predict_noCV.prob refers to a predicted normalized covariance proablility.
"LC" refers to liver cancer and "C" refers to cirrhosis.

The intensity data shown in Table 1 is analyzed by using leave-one-out cross-validation method. The logistic regression model is used in the analysis by using leave-one-out cross-validation method.

Table 2 shows test results using a value obtained the analysis by using leave-one-out cross-validation method, that is, 81.61 TMED (normalized). That is, when the intensity value is equal to or greater than 81.61, the subject is determined to be a liver cancer patient, and when the intensity value is less than 81.61, the subject is determined to be a cirrhosis patient. The results for subjects diagnosed with cirrhosis or liver cancer based on the band intensity values of the integrin-β1 protein measured in the microvesicles separated by using the beads coated with anti-TMED2 antibodies are shown in Table 2 below. The prediction results was tested by using a logistic regression method using a determination function=2.153-0.027*TMED2 which is a probability of a patient to be a liver cancer patient, wherein TMED2 refers to band intensity values of the integrin-β1 protein measured in the microvesicles separated by using the beads coated with anti-TMED2 antibodies, and the subject is determined to be a liver cancer patient when the determination function value is equal to or greater than 0.5, and the subject is determined to be a cirrhosis patient when the determination function value is less than 0.5. The results denote an area under the curve (AUC) of 0.693, sensitivity of 0.692, and specificity of 0.692. FIG. 1 is a graph showing a ROC curve to determine presence of cirrhosis or liver cancer in the sample based on the band intensity values of the integrin-β1 protein measured in the microvesicles separated by using the beads coated with anti-TMED2 antibodies.

TABLE 2

|  | Actual cirrhosis | Actual liver cancer | Total |
|---|---|---|---|
| *Predicted cirrhosis | 9 | 4 | 13 |
| *Predicted liver cancer | 4 | 9 | 13 |
| total | 13 | 13 | 26 |

*"Predicted" cirrhosis or liver cancer is determined by using the value 81.61 obtained by the leave-one-out cross-validation method.

Table 3 shows the band intensity values of the integrin-β1 protein measured in the microvesicles separated by using the beads coated with anti-CD43 antibodies and the predicted co-variances.

TABLE 3

| Sample no. | *intensity | Actual disease state | ***Predict-noCV | ***Predict_noCV.prob |
|---|---|---|---|---|
| 1 | 68.47 | LC | LC | 0.457221 |
| 2 | 0.52 | LC | C | 0.576041 |
| 3 | 16.73 | LC | C | 0.547975 |
| 4 | 17.78 | LC | C | 0.546144 |
| 5 | 17.86 | LC | C | 0.546005 |
| 6 | 24.84 | LC | C | 0.533807 |
| 7 | 95.03 | LC | LC | 0.411347 |
| 8 | 42.01 | LC | C | 0.503657 |
| 9 | 36.38 | LC | C | 0.513557 |
| 10 | 148.09 | LC | LC | 0.324819 |
| 11 | 144.75 | LC | LC | 0.329994 |
| 12 | 20.99 | LC | C | 0.540541 |
| 13 | 9.62 | LC | C | 0.560333 |
| 14 | 88.62 | C | LC | 0.422309 |
| 15 | 21.32 | C | C | 0.539964 |
| 16 | 38.29 | C | C | 0.510199 |
| 17 | 27.86 | C | C | 0.528515 |
| 18 | 15.62 | C | C | 0.549909 |
| 19 | 42.29 | C | C | 0.503165 |
| 20 | 77.70 | C | LC | 0.441156 |
| 21 | 16.52 | C | C | 0.548341 |
| 22 | 74.71 | C | LC | 0.446348 |
| 23 | 17.02 | C | C | 0.547469 |
| 24 | 43.59 | C | C | 0.500878 |
| 25 | 26.10 | C | C | 0.5316 |
| 26 | 22.04 | C | C | 0.538706 |

*"intensity" refers to band intensity values of the integrin-β1 protein measured in the microvesicles separated by using the beads coated with anti-CD43 antibodies.
** Predict-noCV refers to a predicted normalized covariance..
******Predict_noCV.prob refers to a predicted normalized covariance probability.
"LC" refers to liver cancer and "C" refers to cirrhosis.

The intensity data shown in Table 3 is analyzed by using leave-one-out cross-validation method. The logistic regression model is used in the analysis by using leave-one-out cross-validation method.

Figure 2:
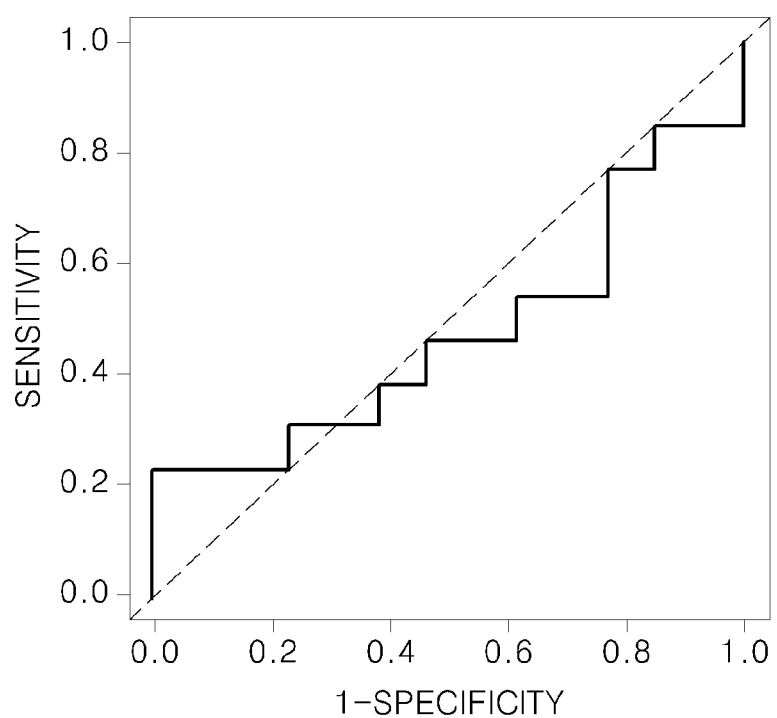
FIG. 2 is a graph showing a ROC curve for determining the presence of cirrhosis or liver cancer in a sample based on band intensity values of protein measured in microvesicles that are separated by using beads coated with anti-cluster of differentiation 43 (CD43) antibodies.

Table 4 shows test results using a value obtained the analysis by using leave-one-out cross-validation method, that is, 68.47 CD43 (normalized). That is, when the intensity value is equal to or greater than 68.47, the subject is determined to be a liver cancer patient, and when the intensity value is less than 68.47, the subject is determined to be a cirrhosis patient. The results for subjects diagnosed with cirrhosis or liver cancer based on the band intensity values of the integrin-β1 protein measured in the microvesicles separated by using the beads coated with anti-CD 43 antibodies are shown in Table 4 below. The prediction results was tested by using a logistic regression method using a determination function=0.31-0.007*CD43 which is a probability of a patient to be a liver cancer patient, wherein CD43 refers to band intensity values of the integrin-β1 protein measured in the microvesicles separated by using the beads coated with anti-CD43 antibodies, and the subject is determined to be a liver cancer patient when the determination function value is equal to or greater than 0.5, and the subject is determined to be a cirrhosis patient when the determination function value is less than 0.5. The results denote AUC of 0. 0.538, sensitivity of 0.308, and specificity of 0.769. FIG. 2 is a graph showing a ROC curve to determine the presence of cirrhosis or liver cancer in the sample based on the band intensity values of the integrin-β1 protein measured in the microvesicles separated by using the beads coated with anti-CD 43 antibodies.

TABLE 4

|  | Actual cirrhosis | Actual liver cancer |  |
|---|---|---|---|
| Predicted cirrhosis | 10 | 9 | 19 |
| Predicted liver cancer | 3 | 4 | 7 |
| Total | 13 | 13 | 26 |

* "Predicted" cirrhosis or liver cancer is determined by using the value 68.47 obtained by the leave-one-out cross-validation method.

Table 5 shows the band intensity values of the integrin-$\beta$1 protein measured in the microvesicles separated by using the beads coated with anti-TMED2 antibodies and anti-CD43 antibodies and the predicted co-variances.

TABLE 5

| Sample no. | *TMED2 intensity | *CD43 intensity | Actual disease state | ***Predict-noCV | ***Predict_noCV.prob |
|---|---|---|---|---|---|
| 1 | 69.84 | 68.47 | LC | C | 0.571654 |
| 2 | 82.4 | 0.52 | LC | LC | 0.471643 |
| 3 | 30.4 | 16.73 | LC | C | 0.789743 |
| 4 | 111.34 | 17.78 | LC | LC | 0.290976 |
| 5 | 114.67 | 17.86 | LC | LC | 0.272554 |
| 6 | 52.16 | 24.84 | LC | C | 0.675877 |
| 7 | 88.74 | 95.03 | LC | LC | 0.448743 |
| 8 | 83.71 | 42.01 | LC | LC | 0.471603 |
| 9 | 138.54 | 36.38 | LC | LC | 0.165346 |
| 10 | 119.96 | 148.09 | LC | LC | 0.266111 |
| 11 | 162.62 | 144.75 | LC | LC | 0.101132 |
| 12 | 39.91 | 20.99 | LC | C | 0.743987 |
| 13 | 105.75 | 9.62 | LC | LC | 0.321978 |
| 14 | 76.06 | 88.62 | C | C | 0.533879 |
| 15 | 62.99 | 21.32 | C | C | 0.607186 |
| 16 | 90.23 | 38.29 | C | LC | 0.4267 |
| 17 | 89.19 | 27.86 | C | LC | 0.431474 |
| 18 | 75.37 | 15.62 | C | C | 0.522938 |
| 19 | 28.89 | 42.29 | C | C | 0.800062 |
| 20 | 78.83 | 77.7 | C | C | 0.51263 |
| 21 | 9.29 | 16.52 | C | C | 0.86999 |
| 22 | 60.3 | 74.71 | C | C | 0.635303 |
| 23 | 86.16 | 17.02 | C | LC | 0.449609 |
| 24 | 62.26 | 43.59 | C | C | 0.616479 |
| 25 | 76.02 | 26.1 | C | C | 0.520749 |
| 26 | 81.61 | 22.04 | C | Liver cancer | 0.481653 |

*"TMED2 intensity" and "CD43 intensity" refers to band intensity values of the integrin-$\beta$1 protein measured in the microvesicles separated by using the beads coated with anti-TMED2 antibodies and anti-CD43 antibodies, respectively.
** Predict-noCV refers to a predicted normalized covariance.
******Predict_noCV.prob refers to a predicted normalized covariance probability.
"LC" refers to liver cancer and "C" refers to cirrhosis.

The intensity data shown in Table 5 is analyzed by using leave-one-out cross-validation method. The logistic regression model is used in the analysis by using leave-one-out cross-validation method.

Figure 3:
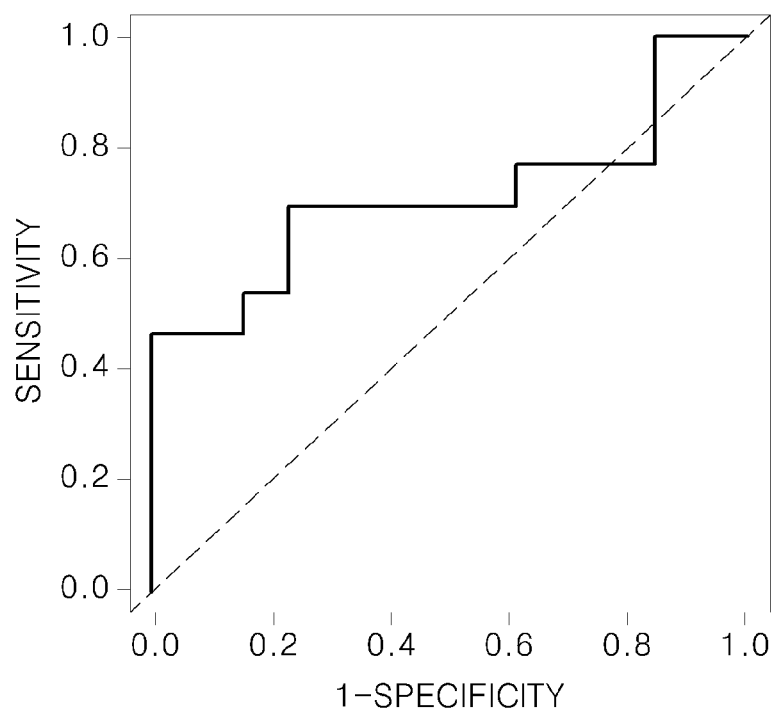
FIG. 3 is a graph showing a ROC curve for determining the presence of cirrhosis or liver cancer in a sample based on band intensity values of protein measured in microvesicles that are separated by using beads coated with anti-TMED2 antibodies and beads coated with anti-CD43 antibodies.

Table 6 shows test results that the prediction was conducted by using a logistic regression method using a determination function=0.31-0.007*CD43 which is a probability of a patient to be a liver cancer patient, wherein CD43 refers to band intensity values of the integrin-$\beta$1 protein measured in the microvesicles separated by using the beads coated with anti-TMED2 antibodies and anti-CD43 antibodies, and the subject is determined to be a liver cancer patient when the determination function value is equal to or greater than 0.5, and the subject is determined to be a cirrhosis patient when the determination function value is less than 0.5. The results of subjects diagnosed with cirrhosis or liver cancer based on the band intensity values of the integrin-$\beta$1 protein measured in the microvesicles separated by using the beads coated with anti-TMED2 antibodies and anti-CD43 antibodies are shown in Table 6 below. The results denote AUC of 0.692, sensitivity of 0.692, and specificity of 0.692. FIG. 3 is a graph showing a ROC curve to determine presence of cirrhosis or liver cancer in the sample based on the band intensity values of the integrin-$\beta$1 protein measured in the microvesicles separated by using the beads coated with anti-TMED2 antibodies and anti-CD43 antibodies.

TABLE 6

|  | Actual cirrhosis | Actual liver cancer | Total |
|---|---|---|---|
| Predicted cirrhosis | 9 | 4 | 13 |
| Predicted liver cancer | 4 | 9 | 13 |
| total | 13 | 13 | 26 |

* "Predicted" cirrhosis or liver cancer is determined by using the probability value 0.5 obtained by a determination function.

The above results demonstrate it is possible to distinguish liver cancer samples from cirrhosis samples by using the TMED2 and CD43 as tumor markers.

Example 2

Selection of Liver Cancer-Specific Protein and miRNA Marker

The presence of a liver cancer-specific protein and a miRNA marker in blood-derived microvesicles was confirmed using samples taken from a patient with cirrhosis and a patient with liver cancer.

Blood samples in a range of 8 ml to 10 ml were each derived from 13 patients with cirrhosis and 13 patients with liver cancer by using BD Vacutainer® Plus plastic whole blood tubes. Then, the blood samples were separately centrifuged at 1300×g at a temperature of 4° C. for 10 minutes, and accordingly plasma was separated therefrom. The separated plasma was then stored at a temperature of −80° C. A plasma sample was prepared by thawing the stored plasma followed by centrifuged at 3000×g at a temperature of 4° C. for 5 minutes so as to use the supernatants, and remove any precipitates.

Three hundred microliters of the plasma sample were mixed with 30 ul of beads (0.8 ug antibodies/bead ul) each coated with anti-CD9 antibodies (R&D Systems), anti-TMED2 antibodies (Santa Cruz Biotechnology), or anti-CD43 antibodies (R&D Systems) by using a test tube (Axygen). Then, the mixture was incubated at room temperature for 4 hours in Grant Bio rotator, and the beads were separated the mixture by using magnetic forces. Next, the separated beads were mixed again with 300 ul of PBS, followed by incubation at room temperature for 3 hours, as a washing step. The antibody-coated beads were prepared as follows: The beads were used to coat protein G on Dynabead M-270 Amine according to a cross-linking reaction using NHS/EDC, and then each antibody was added thereto for the reaction so as to coat thereon by using dimethylpimelimidate. As a result, $2 \times 10^6$ of the beads were contained in 1 ul of PBS.

After the PBS was removed, miRNA was extracted by using a miRNeasy kit according to the manufacturer's instructions. Then, cDNA was synthesized therefrom using a Universal cDNA synthesis kit (Exiqon), and real time PCR was performed thereto by using a SYBR Green master mix kit (Exiqon) according to the manufacturer's instructions. The primer used herein was provided by the manufacturer.

Based on the absorbance value measured at a wavelength in a range from about 483 nm to about 533 nm in RT-PCR, an ROC curve analysis was performed in view of a combination of the absorbance value of mir-210 measured in the microvesicles separated by using the beads coated with the anti-TMED2 (hereinafter "TMED2_hsa.miR.210") and the absorbance value of mir-346 measured in the microvesicles separated by using the beads coated with the anti-CD43 (hereinafter "CD43_hsa.miR.346").

Figure 4:
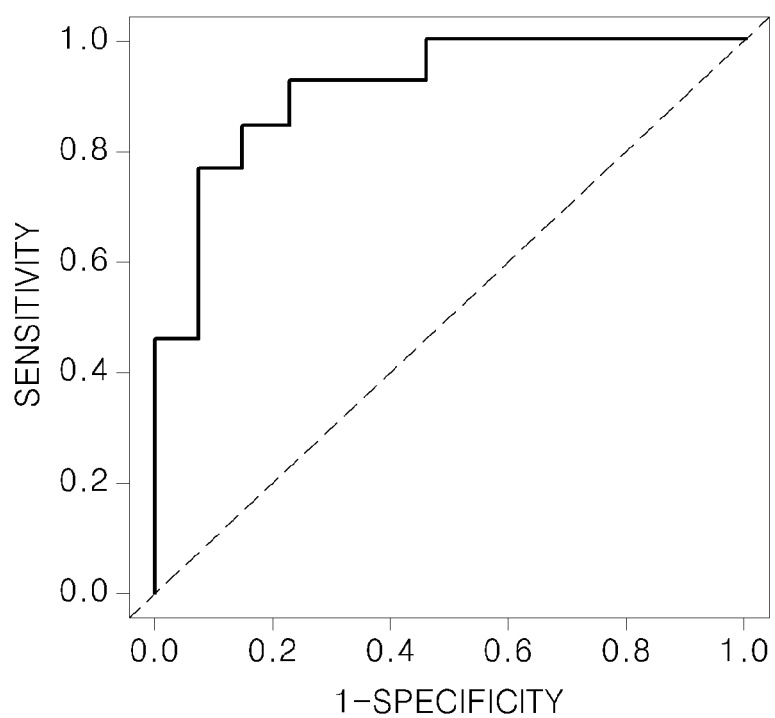
FIG. 4 is a graph showing a ROC curve for determining the presence of cirrhosis or liver cancer in a sample based on the values of mir-210 and mir-346 with respect to the microvesicles that are separated by using beads coated with anti-TMED2 and beads coated with anti-CD43, respectively.

Table 7 shows the band intensity values of the integrin-β1 protein measured in the microvesicles separated by using the beads coated with anti-TMED2 antibodies and anti-CD43 antibodies, TMED2_hsa.miR.210, CD43_hsa.miR.346, and the predicted co-variances.

results denote an area under the curve (AUC) of 0.85, sensitivity of 0.85, and specificity of 0.85. FIG. 4 is a graph showing a ROC curve to determine the presence of cirrhosis or liver cancer in the sample based on the combined values of mir-210 with respect to the microvesicles that were separately by using the beads coated with anti-TMED2 and mir-346 with respect to the microvesicles that were separately by using the beads coated with anti-CD43 and band intensity values of the integrin-β1 protein measured in the microvesicles separated by using the beads coated with anti-TMED2 antibodies and anti-CD43 antibodies, respectively.

TABLE 7

| no. | *TMED2 intensity | *CD43 intensity | CD43_hsa.miR.346 | TMED2_hsa.miR.210 | Actual disease state | ***Predict-noCV | ***Predict_noCV.prob |
| --- | --- | --- | --- | --- | --- | --- | --- |
| 1 | 69.84 | 68.47 | 29 | 26 | LC | LC | 0.083348521 |
| 2 | 82.4 | 0.52 | 29 | 27.2 | LC | LC | 0.053495722 |
| 3 | 30.4 | 16.73 | 30 | 26.4 | LC | LC | 0.295590048 |
| 4 | 111.34 | 17.78 | 30 | 32.5 | LC | C | 0.610961166 |
| 5 | 114.67 | 17.86 | 29.9 | 25.7 | LC | LC | 0.019698477 |
| 6 | 52.16 | 24.84 | 24.5 | 31.1 | LC | LC | 0.074329151 |
| 7 | 88.74 | 95.03 | 27.4 | 30 | LC | LC | 0.207337793 |
| 8 | 83.71 | 42.01 | 29.5 | 30 | LC | LC | 0.421408953 |
| 9 | 138.54 | 36.38 | 24.9 | 30 | LC | LC | 0.004583781 |
| 10 | 119.96 | 148.09 | 28.2 | 27.8 | LC | LC | 0.08253975 |
| 11 | 162.62 | 144.75 | 31 | 27.3 | LC | LC | 0.117406475 |
| 12 | 39.91 | 20.99 | 30.2 | 30.9 | LC | C | 0.859563171 |
| 13 | 105.75 | 9.62 | 30.1 | 30 | LC | LC | 0.279624467 |
| 14 | 76.06 | 88.62 | 30 | 30 | C | C | 0.700420143 |
| 15 | 62.99 | 21.32 | 26.2 | 34.2 | C | C | 0.561792216 |
| 16 | 90.23 | 38.29 | 28.8 | 34 | C | C | 0.801398191 |
| 17 | 89.19 | 27.86 | 31 | 33.9 | C | C | 0.944395352 |
| 18 | 75.37 | 15.62 | 34.1 | 37.1 | C | C | 0.999337077 |
| 19 | 28.89 | 42.29 | 34.9 | 33.5 | C | C | 0.999398551 |
| 20 | 78.83 | 77.7 | 30 | 30.3 | C | C | 0.693412076 |
| 21 | 9.29 | 16.52 | 33 | 30 | C | C | 0.984624826 |
| 22 | 60.3 | 74.71 | 34.6 | 30 | C | C | 0.988915782 |
| 23 | 86.16 | 17.02 | 35 | 26.1 | C | C | 0.708787136 |
| 24 | 62.26 | 43.59 | 34.4 | 31.5 | C | C | 0.992062106 |
| 25 | 76.02 | 26.1 | 29.9 | 27.7 | C | LC | 0.196926618 |
| 26 | 81.61 | 22.04 | 28.8 | 30.4 | C | LC | 0.318642451 |

*"TMED2 intensity" and "CD43 intensity" refers to band intensity values of the integrin-β1 protein measured in the microvesicles separated by using the beads coated with anti-TMED2 antibodies and anti-CD43 antibodies.
***Predict-noCV refers to a predicted normalized covariance.
***Predict_noCV.prob refers to a predicted normalized covariance probability. "LC" refers to liver cancer and "C" refers to cirrhosis.

The intensity data shown in Table 7 is analyzed by using leave-one-out cross-validation method. The logistic regression model is used in the analysis by using leave-one-out cross-validation method.

Table 8 shows test results that the prediction was conducted by using a logistic regression method using a determination function=−38.162+0.012*CD43-0.03*TMED2+ 0.616*TMED2_hsa.miR.210+0.725*CD43_hsa.miR.346 which is a probability of a patient to be a liver cancer patient, wherein CD43 refers to band intensity values of the integrin-β1 protein measured in the microvesicles separated by using the beads coated with anti-TMED2 antibodies and anti-CD43 antibodies, and the subject is determined to be a liver cancer patient when the determination function value is equal to or greater than 0.5, and the subject is determined to be a cirrhosis patient when the determination function value is less than 0.5. The results for subjects diagnosed with cirrhosis or liver cancer based on such band intensity and absorbance value above are shown in Table 8 below. The

TABLE 8

|  | Actual cirrhosis | Actual liver cancer | total |
| --- | --- | --- | --- |
| Predicted cirrhosis | 11 | 2 | 13 |
| Predicted liver cancer | 2 | 11 | 13 |
| total | 13 | 13 | 26 |

* "Predicted" cirrhosis or liver cancer is determined by using the probability value 0.5 obtained by a determination function.

The above results demonstrate it is possible to distinguish a sample of liver cancer from a sample of cirrhosis by using the TMED2 and CD43 as tumor markers as well mir-210 and mir-346 expression values.

As described above, according to the one or more of the above embodiments of the present invention, a composition for diagnosing liver cancer in a subject may have high efficiency. According to one or more of the above embodiments of the present invention, a method of diagnosing liver cancer in a subject may be used to efficiently diagnose liver cancer in a subject. According to one or more of the above embodiments of the present invention, a method of obtaining information for diagnosing liver cancer in a subject may have high efficiency.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of diagnosing liver cancer in a subject, the method comprising:
   contacting a sample from a subject with a substance that specifically binds to transmembrane emp24 domain trafficking protein 2 (TMED2) on the surface of a microvesicle in the sample to provide a mixture of the sample and the substance, wherein the substance is an anti-TMED2 antibody fixed to a solid support, thereby forming a complex between the anti-TMED2 antibody fixed to the solid support and the TMED2 on the surface of the microvesicle;
   separating the complex from the mixture;
   measuring the level of a marker for a microvesicle from the complex in the sample, wherein the marker is a surface protein on the microvesicle selected from the group consisting of CD63, CD83, integrin-beta 1 (ITGB1), CD9, CD36, CD81, EpCAM, caveolin, FasL, HLA-DRA, MUC1, ERBB4, GPER, ERBB2, MLANA, and AMHR2;
   measuring the level of the marker for a microvesicle in a control sample; and
   determining that the subject has a liver cancer when the level of the marker for a microvesicle in the sample is greater than that in the control sample,
   wherein the control sample includes a plurality of samples obtained from cirrhosis patients.

2. The method according to claim 1, wherein the marker for a microvesicle is integrin-β1.

3. The method according to claim 1, wherein the solid support is a magnetic microparticle or a magnetic nanoparticle.

4. The method according to claim 1, further comprising lysing the microvesicle in the complex after the separating step and before the measuring step to produce a lysate of the microvesicle.

5. The method according to claim 4, wherein the measuring step comprises conducting an electrophoresis for the lysate and then western blotting.

6. The method according to claim 5, wherein the anti-TMED2 antibody is attached to a detectable label.

* * * * *

SEQUENCE LISTING

```
<160> NUMBER OF SEQ ID NOS: 6

<210> SEQ ID NO 1
<211> LENGTH: 201
<212> TYPE: PRT
<213> ORGANISM: Homo sapiens

<400> SEQUENCE: 1

Met Val Thr Leu Ala Glu Leu Leu Val Leu Leu Ala Ala Leu Leu Ala
1               5                   10                  15

Thr Val Ser Gly Tyr Phe Val Ser Ile Asp Ala His Ala Glu Glu Cys
            20                  25                  30

Phe Phe Glu Arg Val Thr Ser Gly Thr Lys Met Gly Leu Ile Phe Glu
        35                  40                  45

Val Ala Glu Gly Gly Phe Leu Asp Ile Asp Val Glu Ile Thr Gly Pro
    50                  55                  60

Asp Asn Lys Gly Ile Tyr Lys Gly Asp Arg Glu Ser Ser Gly Lys Tyr
65                  70                  75                  80

Thr Phe Ala Ala His Met Asp Gly Thr Tyr Lys Phe Cys Phe Ser Asn
                85                  90                  95

Arg Met Ser Thr Met Thr Pro Lys Ile Val Met Phe Thr Ile Asp Ile
            100                 105                 110

Gly Glu Ala Pro Lys Gly Gln Asp Met Glu Thr Glu Ala His Gln Asn
        115                 120                 125

Lys Leu Glu Glu Met Ile Asn Glu Leu Ala Val Ala Met Thr Ala Val
    130                 135                 140

Lys His Glu Gln Glu Tyr Met Glu Val Arg Glu Arg Ile His Arg Ala
145                 150                 155                 160

Ile Asn Asp Asn Thr Asn Ser Arg Val Val Leu Trp Ser Phe Phe Glu
                165                 170                 175

Ala Leu Val Leu Val Ala Met Thr Leu Gly Gln Ile Tyr Tyr Leu Lys
            180                 185                 190
```

Arg Phe Phe Glu Val Arg Arg Val Val
         195                 200

<210> SEQ ID NO 2
<211> LENGTH: 2126
<212> TYPE: DNA
<213> ORGANISM: Homo sapiens

<400> SEQUENCE: 2

| | | | | | |
|---|---|---|---|---|---|
| gcggagctta | ggcggcggtg | gctgagaagg | cagcggggcg | gcggcggcgg | cggcggcggc | 60 |
| ggctgtggag | gccgcagtcc | gggtcctggc | ttcggcctca | gccccaccat | ggtgacgctt | 120 |
| gctgaactgc | tggtgcttct | ggccgctctc | ctggccacgg | tctcgggcta | tttcgttagc | 180 |
| atcgacgccc | atgctgaaga | gtgcttcttt | gagcgggtca | cctcgggcac | caagatgggc | 240 |
| ctcatcttcg | aggtggcgga | gggcggcttc | ctggacatcg | acgtggagat | tacaggacca | 300 |
| gataacaaag | gaatttacaa | aggagacaga | gaatccagtg | ggaaatacac | atttgctgct | 360 |
| cacatggatg | aacatacaa | attttgtttt | agtaaccgga | tgtccaccat | gactccaaaa | 420 |
| atagtgatgt | tcaccattga | tattggggag | gctccaaaag | acaagatat | ggaaacagaa | 480 |
| gctcaccaga | acaagctaga | agaaatgatc | aatgagctag | cagtggcgat | gacagctgta | 540 |
| aagcacgaac | aggaatacat | ggaagtccgg | gagagaatac | acagagccat | caacgacaac | 600 |
| acaaacagca | gagtggtcct | ttggtccttc | tttgaagctc | ttgttctagt | tgccatgaca | 660 |
| ttgggacaga | tctactacct | gaagagattt | tttgaagtcc | ggagagttgt | taaaaagcc | 720 |
| tcttcctgat | gatcccaact | cagaattcac | tgtttaccaa | acaccttggt | cataataatg | 780 |
| tcattagttt | ctccattttt | attttctgaa | ctgtacattc | acaacttatg | tttctttgag | 840 |
| attaatagat | attgggggaa | aaacgccttt | ttaggaaaat | tatagtgaaa | atttgacagt | 900 |
| tgattggcat | aatttcttgt | ttgaatgctg | cctccattat | ataggtcctt | ccaggaactc | 960 |
| aaacactgta | agtgaaatat | gggagtatag | ttttttattat | ttcttctttt | cctttttgttt | 1020 |
| tcataatata | atgcagtttg | ttcaggaaat | cagcacaaag | cctgatagta | ctttactaaa | 1080 |
| atgactgcat | tctttggatt | ccttcagtct | atggttcaag | tcactaaaga | ttcattttttg | 1140 |
| ttgagtcctt | atgagaaaca | gcagtatgaa | tcttgacggt | ttctgccccgt | cctaatggca | 1200 |
| gagctctctg | acttgggtgt | atgctgccag | gctgggtact | ttcatacttt | gttttcttgt | 1260 |
| tttgctttaa | aactacgact | cagcatacat | tttcccacat | acattttttac | attgtacctt | 1320 |
| aggactcagt | catctccact | taaattgatg | acacaagcag | ctaataacca | tttctgggtt | 1380 |
| tctgcctaac | cccctaattg | tctgttaaag | ccaattctct | gggtgtccca | gtgagtggtg | 1440 |
| gcttttttttc | tttccacatt | ggcacattca | cttctcccac | tcttggcatg | taagaaataa | 1500 |
| gcatttacat | aattgaaaa | atctggattt | ctgatgccaa | agggttaaag | cttcttggat | 1560 |
| ttcatttcat | tgatatacag | ccactatttt | attttttgatc | agtggccttt | gggccactgt | 1620 |
| tcagggtact | gaccatcagt | gtcagcatta | gggttttggt | ttttgtttct | tttgggtctt | 1680 |
| tctttttttgg | cacatgtgaa | tcttgtttttg | tgtaaaatga | aattactttc | tcttgttctc | 1740 |
| tgatgatggg | tttaaaatta | aaagagcatc | cggttttggt | atggggatga | tccaggatta | 1800 |
| tgttgtgact | gatacatatt | agttacttgt | gcttttttttt | ttttttttttgg | atctttgcaa | 1860 |
| gggcaaaaact | acaagtaacg | agttttatat | aattaattta | aatttgttac | aggttttcat | 1920 |
| gttcaggata | aaccatactt | ccaccttggg | tgagaacact | tgcaacagtt | tattaatgag | 1980 |
| gtgactttca | ccttaggaca | actgttgcat | gccaagtttt | ttgtgtgtgt | gaaacacttc | 2040 |

```
aaaactgatt taaaagatgt aaatttaaaa ttggttgtat ctaatatgcc ccaggttcgg    2100
taaataaaca attctttta aaaaca                                          2126
```

<210> SEQ ID NO 3
<211> LENGTH: 400
<212> TYPE: PRT
<213> ORGANISM: Homo sapiens

<400> SEQUENCE: 3

```
Met Ala Thr Leu Leu Leu Leu Gly Val Leu Val Ser Pro Asp
1               5                   10                  15

Ala Leu Gly Ser Thr Thr Ala Val Gln Thr Pro Thr Ser Gly Glu Pro
            20                  25                  30

Leu Val Ser Thr Ser Glu Pro Leu Ser Ser Lys Met Tyr Thr Thr Ser
        35                  40                  45

Ile Thr Ser Asp Pro Lys Ala Asp Ser Thr Gly Asp Gln Thr Ser Ala
    50                  55                  60

Leu Pro Pro Ser Thr Ser Ile Asn Glu Gly Ser Pro Leu Trp Thr Ser
65                  70                  75                  80

Ile Gly Ala Ser Thr Gly Ser Pro Leu Pro Glu Pro Thr Thr Tyr Gln
                85                  90                  95

Glu Val Ser Ile Lys Met Ser Ser Val Pro Gln Glu Thr Pro His Ala
            100                 105                 110

Thr Ser His Pro Ala Val Pro Ile Thr Ala Asn Ser Leu Gly Ser His
        115                 120                 125

Thr Val Thr Gly Gly Thr Ile Thr Thr Asn Ser Pro Glu Thr Ser Ser
    130                 135                 140

Arg Thr Ser Gly Ala Pro Val Thr Thr Ala Ala Ser Ser Leu Glu Thr
145                 150                 155                 160

Ser Arg Gly Thr Ser Gly Pro Pro Leu Thr Met Ala Thr Val Ser Leu
                165                 170                 175

Glu Thr Ser Lys Gly Thr Ser Gly Pro Pro Val Thr Met Ala Thr Asp
            180                 185                 190

Ser Leu Glu Thr Ser Thr Gly Thr Thr Gly Pro Pro Val Thr Met Thr
        195                 200                 205

Thr Gly Ser Leu Glu Pro Ser Ser Gly Ala Ser Gly Pro Gln Val Ser
    210                 215                 220

Ser Val Lys Leu Ser Thr Met Met Ser Pro Thr Thr Ser Thr Asn Ala
225                 230                 235                 240

Ser Thr Val Pro Phe Arg Asn Pro Asp Glu Asn Ser Arg Gly Met Leu
                245                 250                 255

Pro Val Ala Val Leu Val Ala Leu Leu Ala Val Ile Val Leu Val Ala
            260                 265                 270

Leu Leu Leu Leu Trp Arg Arg Arg Gln Lys Arg Arg Thr Gly Ala Leu
        275                 280                 285

Val Leu Ser Arg Gly Gly Lys Arg Asn Gly Val Val Asp Ala Trp Ala
    290                 295                 300

Gly Pro Ala Gln Val Pro Glu Glu Gly Ala Val Thr Val Thr Val Gly
305                 310                 315                 320

Gly Ser Gly Gly Asp Lys Gly Ser Gly Phe Pro Asp Gly Glu Gly Ser
                325                 330                 335

Ser Arg Arg Pro Thr Leu Thr Thr Phe Phe Gly Arg Arg Lys Ser Arg
            340                 345                 350

Gln Gly Ser Leu Ala Met Glu Glu Leu Lys Ser Gly Ser Gly Pro Ser
```

|  |  |  | 355 |  |  | 360 |  |  | 365 |  |  |
|---|---|---|---|---|---|---|---|---|---|---|---|
| Leu | Lys | Gly | Glu | Glu | Glu | Pro | Leu | Val | Ala | Ser | Glu | Asp | Gly | Ala | Val |
|  |  |  | 370 |  |  | 375 |  |  | 380 |  |  |

| Asp | Ala | Pro | Ala | Pro | Asp | Glu | Pro | Glu | Gly | Gly | Asp | Gly | Ala | Ala | Pro |
| 385 | | | | 390 | | | | 395 | | | | 400 |

<210> SEQ ID NO 4
<211> LENGTH: 6944
<212> TYPE: DNA
<213> ORGANISM: Homo sapiens

<400> SEQUENCE: 4

| agttctcagg ctcacattcc caccacccac tctgagccc agccctccct agcatcacca | 60 |
| cttccatccc attcctcagc caagagccag gaatcctgat tccagatccc acgcttccct | 120 |
| gcctccctca ggtcccagct cttgctcctg cctgtttgcc tggaaatggc cacgcttctc | 180 |
| cttctccttg gggtgctggt ggtaagccca gacgctctgg ggagcacaac agcagtgcag | 240 |
| acacccacct ccggagagcc tttggtctct actagcgagc cctgagctc aaagatgtac | 300 |
| accacttcaa taacaagtga ccctaaggcc gacagcactg ggaccagac ctcagcccta | 360 |
| cctccctcaa cttccatcaa tgagggatcc cctctttgga cttccattgg tgccagcact | 420 |
| ggttcccctt tacctgagcc aacaacctac caggaagttt ccatcaagat gtcatcagtg | 480 |
| ccccaggaaa cccctcatgc aaccagtcat cctgctgttc cataacagc aaactctcta | 540 |
| ggatcccaca ccgtgacagg tggaaccata caacgaact ctccagaaac ctccagtagg | 600 |
| accagtggag ccctgttac cacggcagct agctctctgg agacctccag aggcacctct | 660 |
| ggaccccctc ttaccatggc aactgtctct ctggagactt ccaaaggcac ctctggaccc | 720 |
| cctgttacca tggcaactga ctctctggag acctccactg gaccactgg accccctgtt | 780 |
| accatgacaa ctggctctct ggagccctcc agcggggcca gtggacccca ggtctctagc | 840 |
| gtaaaactat ctacaatgat gtctccaacg acctccacca cgcaagcac tgtgcccttc | 900 |
| cggaacccag atgagaactc acgaggcatg ctgccagtgg ctgtgcttgt ggccctgctg | 960 |
| gcggtcatag tcctcgtggc tctgctcctg ctgtggcgcc ggcggcagaa gcggcggact | 1020 |
| ggggccctcg tgctgagcag aggcggcaag cgtaacgggg tggtgacgc ctgggctggg | 1080 |
| ccagcccagg tccctgagga gggggccgtg acagtgaccg tggagggtc cggggggcgac | 1140 |
| aagggctctg ggttccccga tggggagggg tctagccgtc ggcccacgct caccactttc | 1200 |
| tttggcagac ggaagtctcg ccagggctcc ctggcgatgg aggagctgaa gtctgggtca | 1260 |
| ggccccagcc tcaaagggga ggaggagcca ctggtggcca gtgaggatgg ggctgtggac | 1320 |
| gccccagctc ctgatgagcc gaaggggga gacggggctg cccttaagt gtcggtgaat | 1380 |
| agtgaggctg gaggccggaa tctcagccag cctccagcac cttccctctc accatcccac | 1440 |
| tgccccctcg ctcccatgtt tccacccggc accctgatcc tcacccgaat ctccttttt | 1500 |
| tttttcttt gagacagagt ttcgcttgt cgcccaggct ggagtgcaat gcacgatctc | 1560 |
| agttcactgc aacctctgcc tcctaagttc aggcgattct cctgcctcag cttcccgagt | 1620 |
| aactgagatt acaggcaccc accaccatgc ccagctgctt ttttgtattt ttggtagaga | 1680 |
| tggggtttca ccatgttggc taggctggtc tcaaactcct gacctcaggt gatctacctg | 1740 |
| cctcagcctc ccaaagtgct gagattacag acatgagcct ccgcgccttg cctcctcacc | 1800 |
| cacctcttca ctctgaatcc tcatgaggct tctcagccct ggatttcctg ctgccatcct | 1860 |
| cacccagcac ccacaactag cgcctgggca gggcagggct ggcacctctc aacgtctgtg | 1920 |

```
gactgaatga ataaaccctc ctcatccacc cctatttatc tccatcacca tttcccctc    1980 tttcttgttc ctggaaacgg ctgctgagtc tccatcggcc aaacttatct gccctgtgat    2040
ttctttgaca attctccttt tcccccagaa cccaccctgg gttgaccaga gtctgggaag    2100
aaggacaaga gaacccggca aactccctcc taggattaac tttgtaaagc acccttgccc    2160
tgtagctgca agggctgtgg aacctgggca gcccgcaacc acctttagct ctgggccccc    2220
caggccagcc tggagcatgg ctgggtgggg ccaccagccc atgctctcag gcgggcctgt    2280
gatctttccc agggcacatg gactgtaggc tggccctggc ccacaccacc acactctccc    2340
cagccatgga cagaggcagc cagaggcctc acggtttctc ctccgagttt ctggctgggt    2400
gtagttctca gaaacccag tgcctgcgtg tgtccactcg tgggtgtggt ttgtgtgcaa     2460
gagctgagga tttggcgatg cttgggaggg gtagttgtgg gtacagacgg tgtggggtg     2520 ggaagtggtg cagagactga agagggtcaa cctgggcatg ggggacacag ggactgctga    2580
gaacgtgcgt gtcatctttg ctctgatggg gtggacatag cagaaaatct aactctgtct    2640
gtagccccat acagaatgcc agggtgagca cagtggctgg tgccttta at cccagcactt   2700 tggaaagttg aggcaggagg atcgcttgag cccaggagtt cgagtctgaa gtgagctgtg    2760
attgcaccac tgcacttcag cctgggcaac agagtgagcc cctgtctcaa aaagaaaag    2820 aaaaagaaag ccaggcttca tggaaagatc gtatgtgtga cccaaatatg agttcttcag    2880
ctcagccatg gtaatccctt ccttgaagtc tccatttctg cagtacacat gcatgtgcgc    2940
tctctctctc tctctctctc tcacacacac acacacacac acacacacac gcgcgcgcgc    3000
gcgcgctctc ctgcgaacag aggcagggg agaggggttt gccctggtct cggggactgg    3060
tctggctggc gcttcccac tgcacgtttc caggtttagt ttgtctgtgt ctcctcttcc     3120
atcccagggg ctgagcccct tccatcctcc aagaggaacc agtgagagtg agtgaaggag    3180
gggcctggag ccagggactt cccctgtggg gcctgggtgg agaggggaga actcaatggt    3240
gctgcctttg agaccagccc aggctacagc ccaggagcac acatgggcca gggcagttgg    3300
tatttcccga ggacaaagag gaaattttca agaggaagt tgttgagtta gagcttgcgg     3360
tggctgagag cagacaggtt gacctgcaaa aaagacagg ggaggcatgt gagtgtgaca     3420
gccctgctct gtggcctggg caggagatgg gggaagggt caggtggggg atgggctcgt     3480
gcagtgggag aggagacgga gggagggagc gggaagggc ttgcttagtg ggtgggaaga     3540
gctgagctcg gatggaacca gcttctacca gccaggctgg gcaccactg gctgcatct      3600 ggtggccttt tctgattgct atttggactc actgcagctg cagaatgaca gaggccatgt    3660
ccaaaatccc ttagagacac tgttgtctta gagttgttaa ataagagcc cccatatcag     3720 gtttagaaaa tactgtcacc gaacgaacgt cgctgtcctc agctccacct cccttttcctt   3780 tgacagatat ggttgttttc taagccagga ctggtttag tcaggtcctg gcgaatcct      3840 gaaaaaaaga ggtagtacgg gtaaggaagg cacccaacag ggctttcaca atccagaaaa    3900
tatcaaaata taagtgttaa aagagaggca caggccgggt gcggtggctc acgcctgtaa    3960
tctcagcact ttgggaggcc aaggtgggca gatcatgagg tcaggagttt gagaccagcc    4020
tggccaatat gatgaaaccc cgtttctact aaaaatacaa aagttagcca ggcatggtgg    4080
tgtgctcctg taatcccagc tacttaggag gctgaggcca gagaattgct tgaaccctgg    4140
agtcagaggt tgcagtgagc cgggatcatg ccactgtact ccaggctggg tgacaaagtg    4200
agactgtctc aaaaaataaa aataaataaa ataaataaaa gagaggcaca aacagtgtta    4260
```

```
tgaatgcacc aaggaaaatg gtgcattcat aactctcagg tgaagcctac caagccatgc    4320
gtgtgtgcac atatgtgtgt acgtgtgcat gtgcgtgcgt gcatgtgcgt gcgtgcatgt    4380
gcctgtgtgt gtatgtgtgc acatgtgtgt gcgcatgtgt gtgtgtgcgc gcatgtgtgt    4440
gtgcatgcat gttctcccat gcatgtgtac tgtggcaagg gagactttga ggaagagatt    4500
ccagtggctg agcagaaggg ctcgcattgc cctggcgaaa ggttggaagg cttcacctga    4560
gagtgtgtcg tggcctttgt catatccact gcttgattcc tttctttaaa aattattttt    4620
attgttttct acatatgaga accaccacac ctggctaatt tttgtatttt ttgtagagat    4680
ggggtttcac catgttgtcc cggctggtct caaactcccg ggcacaagag atccacctgc    4740
ctcagcctcc caaaatgctg ggactatagg catgagccac tgcacccagc cactgcttca    4800
ttcctggtgg ctgctgtgcc tggcatgttg cagatcctcc atgaatatgc atttgaatga    4860
atgaatgaat gaatgaatga atgaatggag atgacgcctc agagattctt tcttttgaga    4920
tgaggtctca ttctgtcacc cagactagag ggcagtggtg caatcacagc tcaccacagc    4980
ctcaacctcc tgggcctccc aagtagctgc gatcacaggt gtgcaccaac atgcccagct    5040 aattttttt tttaattttt aatttgtaca gacagggtct tgctgtgttg cccaggctgg    5100
tctcaaactc ctgggctcaa gtggtcctcc caccctaagct tccccaaata ctgggattat    5160
aggtgtgagc cactgtgccc aggcttgcct cagatatttg aaggctggga aggattttgc    5220
aaagctggga aaaggaaaag gcattcccag cagaggggat agcaggtgga aatacataat    5280
taaaaaaaaa aaacgtggag cagatccagc gcagtggctc atgcctgtaa tcccagcact    5340
ttgggaggca gagcagggag gattgcttga gtctaggagt tcaagaccag cctgggtaac    5400
atagaaagac cctgtctcta caaaaacaca aaaaattagc caggcgtggt ggtgcatgcc    5460
tgtagtacca gctacttgag aagctgaggc aggaggactg cttgaagcca ggagtttgag    5520
accagcctgg gcaacatagt gagacccccgt gtctacaaaa agtaaacatt tatatatata    5580 tttttttaaag tggagcagtt caatatagag tctttttga acaaacgtga aatagatgtc    5640
tttttttttt ttttgagatg gagttttcac tcttgttacc caggctggag tgcaatggcg    5700
tgatcttggc tcaccagaac ctccgcctcc tgggttcaaa caattctcct gcctcagcct    5760
cccaggtagc tgggattaca ggcatgcacc accaaacccg gataattttg tattttagt    5820 agagatgggg tttcaccatg ttggtcaagc tggtcttgaa ctcccgacct ctgctgatcc    5880
gtatgcctcg gcctcccaaa gtgctgggat tacatgcgtg agccaccgtg cccgacaata    5940
gatgtctttt aattttctgg aggaaaaagc aaagcaaaag aagcagtgga tattttaaga    6000
ctaaaaggaa aaacaaaaaa aggagataga gcaggccaga cgtggtggct caacgtctgt    6060
aatcccagca ctttgggagg ccgaggcagg tggatcacct gaggtcagga gttcaagacc    6120
agcctgacca acatggtgaa accctgtttc aaaatacaaa aaattagctg ggcgtggtgg    6180
cgggcacctg taatcccagc tacttgggag gctgaggcag gagaatccct tgaacccagg    6240
aggtggaggt tgcagtgagc cgagatcacg ccattgcact ccagcctggg cgacaagtaa    6300
aaaactccat ctcaaaaaaa aaaaggaga tagagcaagg aacagtaaga aaatagttgg    6360
gtgcagtggc tatgcggtgg cactatagga ggctgaggcg ggcagatcac ctgaggtcag    6420
gagttggaga ccagcctggg caacatagac ccctatctct acaaaaaatt tgaaatatga    6480
aaaattagcc aggtgtagtg gtgtgcgcct gtggtaccag ctactcaaga ggcgaaggca    6540
gggaagattg cttgagccca ggagtttgag gctatagtga gctgtgatca tgccactgca    6600
ctccagcctg ggcaatagtg tgagactctg tctcaaaaga aagaacatgg ccaggcgtgg    6660
```

```
tggctcacac ctgtaatccc agcactttgg gaggccgagg cagtcagatc atgaggccag    6720
tttgaaacca gcctggccaa catggtgaaa ccctgtctct actaaaaata caaaaattag    6780
ccaggcgtgg tggcatgccc ccgtaatccc agctacttgg gggtctgagg cagaagaatt    6840
gcttgaaacc gggaggcaga ggttgcagtg agccgagatc gtgtcattgc actctagtct    6900
gggcgacaga gcaagactcc gtcttggaaa aaaatttaaa aaaa                      6944

<210> SEQ ID NO 5
<211> LENGTH: 22
<212> TYPE: RNA
<213> ORGANISM: Homo sapiens

<400> SEQUENCE: 5
cugugcgugu gacagcggcu ga                                              22

<210> SEQ ID NO 6
<211> LENGTH: 23
<212> TYPE: RNA
<213> ORGANISM: Homo sapiens

<400> SEQUENCE: 6
ugucugcccg caugccugcc ucu                                             23
```